(12) United States Patent
Handberg (10) Patent No.: US 9,372,190 B2
(45) Date of Patent: Jun. 21, 2016

(54) METHOD OF EVALUATION OF THE RELATIVE RISK OF DEVELOPING ATHEROSCLEROSIS IN PATIENTS

(75) Inventor: Aase Handberg, Risskov (DK)

(73) Assignee: Region Nordjylland, Aalborg Ost (DK)

( * ) Notice: Subject to any disclaimer, the term of this patent is extended or adjusted under 35 U.S.C. 154(b) by 1711 days.

(21) Appl. No.: 11/597,543

(22) PCT Filed: May 26, 2005

(86) PCT No.: PCT/DK2005/000352
§ 371 (c)(1),
(2), (4) Date: Jan. 15, 2008

(87) PCT Pub. No.: WO2005/116644
PCT Pub. Date: Dec. 8, 2005

(65) Prior Publication Data
US 2008/0280376 A1    Nov. 13, 2008

Related U.S. Application Data

(60) Provisional application No. 60/601,123, filed on Aug. 13, 2004.

(30) Foreign Application Priority Data

May 26, 2004  (DK) ................... 2004 00829
Aug. 13, 2004  (DK) ................... 2004 01222

(51) Int. Cl.
*G01N 33/566* (2006.01)
*G01N 33/68* (2006.01)
*C07K 16/28* (2006.01)

(52) U.S. Cl.
CPC .......... *G01N 33/566* (2013.01); *G01N 33/6893* (2013.01); *C07K 16/2896* (2013.01); *G01N 2333/70596* (2013.01); *G01N 2800/32* (2013.01); *G01N 2800/323* (2013.01); *G01N 2800/50* (2013.01); *G01N 2800/52* (2013.01); *G01N 2800/56* (2013.01)

(58) Field of Classification Search
CPC .. C07K 16/28; C07K 16/2896; G01N 33/566; G01N 33/6893; G01N 2333/70596; G01N 2800/32; G01N 2800/323; G01N 2800/50; G01N 2800/52; G01N 2800/56
USPC ............ 435/7.1, 7.2, 7.24, 7.4, 7.5, 7.8, 7.92, 435/7.94, 7.95, 975; 436/518, 528, 536, 436/164, 172; 530/388.22, 388.7, 389.6, 530/391.3
See application file for complete search history.

(56) References Cited

U.S. PATENT DOCUMENTS 5,811,250 A * 9/1998 Solum et al. ............... 435/7.21
6,040,147 A * 3/2000 Ridker et al. .............. 435/7.24
6,322,976 B1   11/2001 Aitman et al.
6,812,023 B1 * 11/2004 Lamparski et al. ........... 435/325
2004/0076621 A1 * 4/2004 Watt ........................ 424/93.21

FOREIGN PATENT DOCUMENTS

| EP | 2000180447 | | 6/2000 |
| EP | 2001056338 | | 2/2001 |
| JP | 2000-180447 | * | 6/2000 |
| WO | 0136675 A2 | | 5/2001 |
| WO | 2004017986 A1 | | 3/2004 |

OTHER PUBLICATIONS

Goding, 1983. Monoclonal Antibodies: Principles and Practice, Academic Press, London. pp. 250-261.*
Tandon et al., 1989. Isolation and characterization of platelet glycoprotein IV (CD36). J. Biol. Chem. 264: 7570-7575.*
Burns et al., 1992. Platelet microparticle binding to leukocytes is inhibited by antibodies to GMP-140 and by sulfated glycans. Platelets 3: 271-279.*
Nomura et al., 1995. Platelet-derived microparticles may influence the development of atherosclerosis in diabetes mellitus. Atherosclerosis 116: 235-240.*
Pelsers et al., 1999. A sensitive immunoassay for rat fatty acid translocase (CD36) using phage antibodies selected on cell transfectants: . . . Biochem. J. 337: 407-414.*
Villmow et al., 2003. Markers of platelet activation and platelet-leukocyte interaction in patients with myeloproliferative syndromes. Thrombosis Res. 108: 139-145.*
Handberg et al., 2006. Indentification of the oxidized low-density lipoprotein scavenger receptor CD36 in plasma: a novel marker of insulin resistance. Circulation 114 : 1169-1176.*
Glintborg et al., 2008. Soluble CD36 and risk markers of insulin resistance and atherosclerosis are elevated in polycystic ovary syndrome and significantly reduced during pioglitazone treatment. Diabetes Care 31: 328-334.*
Handberg et al., 2008. Soluble CD36 in plasma is increased in patients with symptomatic atherosclerotic carotid plaques and is related to plaque instability. Stroke 39 : 3092-3095.*
Anonymous, 2010. Santa Cruz Biotechnology Datasheet: CD36 sc-5522. Available for downloading at www.scbt.com.*
Anonymous, 2010. Santa Cruz Biotechnology Datasheet: CD36 sc-7309. Available for downloading at www.scbt.com.*

(Continued)

*Primary Examiner* — Gail R Gabel
*Assistant Examiner* — James L Grun
(74) *Attorney, Agent, or Firm* — Cooley LLP (57) ABSTRACT

The present invention relates to a method for determining the amount of circulating CD36 protein or a fraction thereof which is present in cell-free plasma, preferably in a high molecular weight plasma fraction, such as a lipoprotein fraction selected from Low Density Lipoprotein, Intermediate Density Lipoprotein, and Very Low Density Lipoprotein using an immunological method which comprises the steps of (i) providing a plasma sample to be investigated, (ii) providing an anti-CD36 antibody, (iii) exposing the sample to be investigated to the antibody, and (iv) detecting and quantifying the amount of CD36 which binds to the antibody.

11 Claims, 10 Drawing Sheets

(56) References Cited

OTHER PUBLICATIONS

Anonymous, 2010. Santa Cruz Biotechnology Datasheet: CD36 sc-9154. Available for downloading at www.scbt.com.*

Viles-Gonzalez et al., 2004. Atherothrombosis: a widespread disease with unpredictable and life-threatening consequences. European Heart Journal 25: 1197-1207.*

Novatein Biosciences, 2014, "Human CD36 ELISA Kit, Catalog No. NS-E10032", downloaded from www.novateinbio.com/en/index.php?controller=attachment?id_attachment=78 on Jul. 15, 2015.*

Stampfer et al., 1991. A prospective study of cholesterol, apolipoproteins, and the risk of myocardial infarction. New England J. Med. 325: 373-381.*

* cited by examiner

CD36 in FPLC fractions of human plasma

| Apo B | 0.08 | 0.01 |
| ApoA | 0.01 | 0.08 |

METHOD OF EVALUATION OF THE RELATIVE RISK OF DEVELOPING ATHEROSCLEROSIS IN PATIENTS

The present invention relates to a method of quantification of CD36 protein or a fragment thereof in a patient plasma sample using a specific antibody based assay and the correlation of the thus measured level of CD36 with the relative risk of said patient developing a disease state, such as atherosclerosis, atherothrombosis and insulin resistance. Further aspects of the invention are related to a method of predicting the development of a disease state, such as atherosclerosis or atherothrombosis in a human suffering from diabetes and/or obesity, and a diagnostic kit for detection of CD36 in blood plasma and/or quantification of the relative level of CD36 in blood plasma.

BACKGROUND

Worldwide the incidence of diabetes mellitus type 2 (DM2) is increasing and present an ever growing factor of expenditure in the health systems of especially the western world. At the time of diagnosis about 50% of these patients exhibit complications, especially in the form of atherosclerosis. The development of atherosclerosis and atherothrombosis may be delayed by intensive treatment of dyslipidemia, insulin resistance and dysrequlation of diabetes as well.

Typically, risk factors for atherothrombosis in diabetes patients are monitored on blood samples such as measurements of the regulation of diabetes (HbA1c) combined with measurements of cholesterol fractions and triglycerides (dyslipidemia). ECG, sensitive CRP, and marker enzymes of heart ischemia are used for screening of cardiac atherosclerosis and thrombosis as well as for diagnostic and monitoring purposes.

Additionally, it is necessary to evaluate clinical symptoms of atherosclerosis thus involving a complex range of tests and clinical evaluations in order to obtain a realistic assessment of the risk factors.

An integrated measurement of the level and risk of atherosclerosis and/or atherothrombosis in patients, such as diabetes patients, would facilitate and enable early intervention thus providing considerable health and economic gains.

Griffin, E. et al. (Nature Medicine, Vol. 7, No. 7, July 2001, pp 840-846) have shown that a glucose mediated increase in CD36 mRNA translation efficiency results in increased expression of the macrophage scavenger receptor CD36 and that expression of CD36 was increased in endarterectomy lesions from patients with a history of hyperglycemia. Thus, the increased translation of CD36 transcripts under high glucose conditions provides a mechanism for accelerated atherosclerosis in diabetics. Griffin et al. use immunocytochemistry on human carotid artery lesions and human peripheral blood mononuclear cells to detect the levels of CD36 expression.

Liang C-P et al.(JCI113:763-73, 2004) found, in a study using macrophages from ob/ob mice, evidence that an increased CD36 protein expression in insulin resistant macrophages is caused by defective insulin signalling, and that defective macrophage insulin signalling predisposes to foam cell formation and atherosclerosis in insulin-resistant states. JP published patent application No. 2000180447 describes a method and a reaction kit for detecting a CD36 antigen in an organism sample such as blood as a marker for the presence of and/or the degree of acute myocardial infarction. However, a correlation between the presence of CD36 antigen in a blood sample of a patient or subject and a risk of said patient or subject developing atherosclerosis is not shown or mentioned in JP 2000180447.

Moreover, it is known that a drop in the CD36 levels in cells of a patient after initiating protease inhibitor therapy relative to the level prior to protease inhibitor therapy is predictive of the subsequent development of lipodystrophy associated with antiretroviral therapy. The level of CD36 is measured in cells using flow cytometric analysis. The cells may be monocytes from a blood sample or a fraction thereof (CA patent application No. 2289365).

Thus, it appears that measurements of the membrane bound CD36 protein as a marker molecule for atherosclerosis related conditions has a diagnostic potential. However, with the present state of the art, such measurements will involve the use of immunocytochemistry and/or flow cytometry which require the use of complicated apparatuses and which are not readily useful for a standard hospital laboratory.

There is a need for a simple and cost efficient method to predict those at risk of developing atherosclerosis and/or atherothrombosis. Said method would provide an integrated measurement of the influence of several risk factors in one analysis of a blood plasma sample by measuring the level of a circulating analyte such as an unbound protein or fraction thereof or soluble complex comprising said protein or fraction present in blood plasma.

SUMMARY OF THE INVENTION

The present invention aims at providing a method which integrates a measurement of the influence of several risk factors in one analysis of a blood plasma sample by measuring the level of circulating CD36 protein or non-cell bound CD36 protein present in blood plasma. The circulating CD36 protein may be present as the unbound (soluble) protein or a peptide fraction thereof, or the CD36 protein may be present bound to a lipoprotein fraction such as Low Density Lipoprotein (LDL), IDL (Intermediate Density Lipoprotein or VLDL (Very Low Density Lipoprotein in a high molecular weight (MW) fraction of the blood plasma, or may be present in microparticles shed from cells such as platelets, monocytes or adipocytes after triggering by various stimuli. Thus, in one aspect the invention provides an immunological method for measuring the amount of circulating CD36 protein in a cell-free plasma sample, comprising the steps of:

(i) providing a plasma sample to be investigated,
(ii) providing an anti-CD36 antibody,
(iii) exposing the sample to be investigated to the anti-CD36 antibody bound to a solid phase,
(iv) optionally exposing the CD36-antibody complex to a second anti-CD36 antibody, and
(iv) detecting and quantifying the amount of the antibody which binds to CD36. Preferably, the circulating CD36 protein or an antibody detectable fraction thereof is bound to a lipoprotein fraction, which may be a Low Density Lipoprotein, an Intermediate Density Lipoprotein, and/or a Very Low Density Lipoprotein which is preferably present in a high molecular weight plasma fraction in a cell-free plasma sample that can be obtained from a subject or patient: Alternatively, the CD36 protein may be present in microparticles shed from cells such as platelets, monocytes or adipocytes after triggering by various stimuli.

In other aspects the invention provides a reagent kit for carrying out the immunological method, and a method of predicting the development of atherosclerosis and/or atherothrombosis in a patient comprising the steps of : (a) obtaining a cell-free plasma sample from said patient, (b) contacting the sample with an anti-CD36 antibody to obtain a CD36-antibody complex; (c) incubating said sample with said antibody to obtain a CD36-antibody complex, (d) contacting said complex with a labelled compound having specific affinity for said complex; and (e) detecting labelled compound bound to said complex, whereby the amount of CD36 protein may be measured; (f) determining whether CD36 levels measured in step (e) are above the standard levels as measured on a healthy reference population, the increase in the level of circulating CD36 being predictive of the risk of the patient developing a disease state, such as atherosclerosis and/or atherothrombosis.

DETAILED DESCRIPTION OF THE INVENTION

In a more specific aspect of the invention there is provided a method for determining human CD36 in a plasma sample by solid phase ELISA enzyme immunoassay which comprises the steps of
(i) providing a plasma sample to be investigated,
(ii) providing an anti-CD36 antibody as defined herein,
(iii) exposing the sample to be investigated to a solid phase and the antibody, and
(iv) detecting and quantifying the amount of the antibody which binds to CD36; and in a more preferred aspect of the invention there is provided a method for determining human CD36 in a plasma sample by solid phase ELISA enzyme immunoassay which comprises the steps of
(i) providing a plasma sample to be investigated,
(ii) providing an anti-CD36 antibody,
(iii) exposing the sample to be investigated to the anti-CD36 antibody bound to a solid phase,
(iv) optionally exposing the CD36-antibody complex to a second anti-CD36 antibody, and
(iv) detecting and quantifying the amount of the antibody which binds to CD36,
and wherein the solid phase preferably is a microtiter plate, the CD36 is preferably present (part of) in a high molecular weight plasma fraction said high molecular weight plasma fraction preferably being a CD36-lipoprotein complex; said anti-CD36 antibody is preferably selected from the group consisting of monoclonal antibodies as specified above and including sc7309 (CD36 (SMf), mouse IgM), and polyclonal CD36 specific antibodies, such as sc5522 (CD36 (N-15), goat IgG, epitope N-terminus (h)), sc9154 (CD36(H-300), rabbit IgG, epitope 1-300 (i)); said determination is preferably carried out by a solid phase enzyme immunoassay, wherein, in the enzyme immunoassay, the sample is exposed to a first, human CD36-binding antibody, and the amount of bound CD36 is measured using a second antibody carrying an enzyme label, where the measurement is carried out by an enzyme-catalyzed colour reaction or chemiluminescence.

CD36 is a 471 amino acid, transmembrane protein (having 1 or 2 membrane spanning domains at amino acid residue positions 439-460 and possibly 7-28). CD36 is a highly glycosylated, 88 kDa glycoprotein with palmitoyl binding sites. CD36 is present in caveolae where it may play a role in the mediation of cellular cholesterol movement into and out of cells. CD36 is expressed by monocytes, macrophages, platelets, microvascular endothelial cells, mammary gland epithelium, adipocytes and muscle tissue. It is a multifunctional receptor that binds to oxidised LDL (OxLDL), long chain fatty acids (LCFA), anionic phospholipids, apoptotic cells, thrombospondin (TSP), collagen and Plasmodium falciparum-infected erythrocytes.

CD36 has numerous cellular functions. It is a Fatty Acid Translocase (FAT) and belongs to the scavenger receptor Class B family, playing a major role in the uptake of Long Chain Fatty Acids (LCFA) over the cell membrane in metabolically active tissue, in foam cell formation, and in uptake of OxLDL by macrophages. The lipid-rich macrophages are then differentiated into foam cells and contribute to the formation of atherosclerotic lesions. In addition, CD36 of macrophages, together with TSP and the integrin alphavbeta3, can phagocytose apoptotic neutrophils. Furthermore, the protein is one of the receptors of collagen in platelet adhesion and aggregation. CD36 can also mediate cytoadherence of Plasmodium falciparum-infected erythrocytes to the endothelium of post-capillary venules of different organs. Moreover, cytoplasmic CD36 plays an important role in signal transduction by interacting with Src family tyrosine kinases. Deficiency in CD36 in Asian and African populations has been associated with insulin resistance.

Monty Krieger (July 1999) Vol. 68, pp. 523-558(doi: 10.1146/annurev.biochem.68.1.523) states that the risk for cardiovascular disease due to atherosclerosis increases with increasing concentrations of low-density lipoprotein (LDL) cholesterol and is inversely proportional to the levels of high-density lipoprotein (HDL) cholesterol. In mice, SR-BI plays a key role in determining the levels of plasma HDL cholesterol and in mediating the regulated, selective delivery of HDL-cholesterol to steroidogenic tissues and the liver. Significant alterations in SR-BI expression can result in cardiovascular and reproductive disorders. SR-BI may play a similar role in humans; thus, modulation of its activity may provide the basis of future approaches to the treatment and prevention of atherosclerotic disease. In addition, Tunstall, R. J. et al. (Am J Physiol Endocrinol Metab 283: E66-E72, 2002, (first published Mar. 12, 2002; 10.1152/ajpendo.000475.2001.) found that after 9 days of exercise there was a significant (36%, P 0.04, treatment effect) increase in skeletal muscle FAT/CD36 human gene expression compared with the untrained state.

Known features of CD36 as of October 1999 have been summarized by Laurence M. Howard; J. L. McGregor, cf. URL www.ncbi.nlm.nih.gov/prow/guide/1625576610_g.htm a part of which is reproduced below:

Alternate names for CD36 (Cluster Determinant 36) include CD36 [HUGO gene name], GPIIIb, GPIV, OKM5-antigen, and PASIV.

Biochemical activity of CD36 includes:
  Recognition of oxidized low density lipoprotein, long chain fatty acids, anionic phospholipids, collagen types I, IV and V, thrombospondin (TSP) and *Plasmodium falciparum* infected erythrocytes, recognition of apoptotic neutrophils in co-operation with TSP and avb3.

The cellular function of CD36 includes: Scavenger receptor for oxidized LDL and shed photoreceptor outer segments;
  Recognition and phagocytosis of apoptotic cells;
  Cell adhesion molecule in platelet adhesion and aggregation, platelet-monocyte and platelet-tumor cell interaction;
  Cytoadherence of *Plasmodium falciparum*-infected erythrocytes;

Disease relevance of CD36 and function of CD36 in intact animal:
  Atherogenesis: Attachment to the vessel wall, infiltration and macrophage foam cell formation;
  Malaria: Cytoadherence of infected cells to microvascular endothelial cells is an important factor in the virulence of cerebral malaria;
  Inflammation: Resolution of inflammation by phagocytosis of aged PMN;
  Vision: CD36-mediated phagocytosis of rod outer segment cells is thought to be critical for normal visual function:
  CD36 deficiency: Naka-negative individuals do not express CD36 on their platelets (type II variant) or on their platelets and monocytes (type I variant) (Yamamoto et al. 1994). This may be predominantly due to a Pro90 to Ser substitution mutation, but as yet no physiological problems have been associated with this deficiency Molecular families in which CD36 is a member:
  CD36—>SR-B class—>host defence scavenger receptors—>scavenger receptor superfamily
  Molecular structure of CD36:
  471 amino acid residues;
  Transmembrane region (residues 439-465) and,
  438 amino acid amino-terminal region may be entirely extracellular or may have a second potential transmembrane region near the amino terminal end;
  aa short cytoplasmic tail (residues 466-471);
  Within the extracellular region resides a hydrophobic region which probably associates with the outer cell membrane (residues 184-204).

The molecular mass of CD36 is reported to be dependent on celltype as shown below:
  Platelets 88 kDa/113 kDa
  Fetal Erythrocytes 78 kDa
  Mammary epithelial Cells 85 kDa
  Erythroleukeimic 88 kDa, 85 kDa, 57 kDa 8
  HeLa 85 (160) kDa 85 kDa
  Dermal Microvascular endothelial cells 80-90 kDa In post-transcriptional modification of CD36 two alternate CD36 mRNA forms have been identified. The first is expressed in HEL cells and omits amino acid residues 41-143. The second has not yet been translated but in which the last 89 residues have been omitted.

Post-translational modification of CD36:
  CD36 is purported to be heavily glycosylated, with 10 N-linked glycosylation sites in the extracellular portion. Glycosylation has been suggested to confer its resistance to proteolytic cleavage;
  Threonine 92 has been shown to be phosphorylated;
  CD36 is also palmitoylated on both N- and C-terminal cytoplasmic tails.

Proteins and DNA elements which regulate transcription of CD36 molecule:
  Oct-2: The first gene shown to be regulated by the Oct-2 transcription factor during B cell differentiation;
  PEBP2: The PEBP2/CBF transcription factors may be important for the constitutive expression of CD36 in monocyte;
  CBF: The PEBP2/CBF transcription factors may be important for the constitutive expression of CD36 in monocyte.

Substrates for CD36 are unknown. It may be possible that CD36 regulates autophosphorylation of residue Thr92. Enzymes which modify CD36 are unknown. It may be possible that Thr92 is phosphorylated by extracellular threonine kinase(s).

Intracellular signalling is probably associated with phosphorylation of Fyn, Lyn and Yes, but the manner by which the cytoplasmic tail interacts with these PTKs is unknown.

Main cellular expression of CD36:

CD36 is expressed on platelets, mature monocytes and macrophages, microvascular endothelial cells, mammary endothelial cells, during stages of erythroid cell development and on some macrophage derived dendritic cells, muscle cells, and adipocytes.

The physiological events regulated by CD36 ligation are still very much unknown. Up to 50% of oxidized LDL are ingested through CD36, thus CD36 appears to be a major scavenger receptor. However, given the apparent absence of disease states in CD36 deficient subjects, other mechanisms appear to be capable of compensating for its absence.

CD36-specific monoclonal antibodies [NAME (Workshop Ids)SOURCE or REFERENCE]:

185-1G2 Vilella
131.1 Tandon, Rockville
131.2 Tandon, Rockville
131.4 Tandon, Rockville
131.5 Tandon, Rockville
131.7 Tandon, Rockville
NAM28-8C12 Blanchard, Nantes
AmAK-5 Kehrel, Muenster
CLB-IVC7 CLB, Amsterdam
Lyp 10.5 McGregor, Lyon
Lyp 13.10 McGregor, Lyon The anti-CD36 antibody used herein may be a monoclonal antibody as described above, and is preferably an isolated polyclonal antibody, obtainable by an immunization process in which purified or recombinant human CD36 is used as antigen component and the antibody is preferably specific for various fractions of the CD36 protein which is present in human blood plasma in soluble form, optionally as a part of a CD36-lipoprotein complex, such as CD36 or a fraction thereof bound to Low Density Lipoprotein (LDL), IDL (Intermediate Density Lipoprotein or VLDL (Very Low Density Lipoprotein) which may be present in a high molecular weight fraction of cell-free plasma. That the plasma is cell-free may be verified microscopically following centrifugation of the blood sample at 3000G. Suitable plasma preparations may be plasma from heparin-stabilized blood, Citrate stabilized or EDTA-stabilized blood. Examples of antibodies useful in the invention are sc5522 and sc9154 (both from Santa Cruz Biotechnology Inc., Santa Cruz, Calif., USA). The antibodies used in the ELISA assay for detection of circulating CD36 in plasma are preferably labelled for ease of detection, the label preferably being in the form of a biotinylation which is well known to a person skilled in the art.

In the context of the present invention, "immunological methods" are understood as meaning analytical methods based on immunochemistry, in particular on an antigen-antibody reaction. Examples of immunological methods include immunoassays such as radioimmunoassay (RIA), enzyme immunoassay (EIA, combined with solid-phase technique: ELISA (Enzyme Linked Immuno Sorbent Assay)) or else immunofluorescence assays. The immunoassay is carried out by exposing the sample to be investigated to a CD36-binding antibody and detecting and quantifying the amount of CD36 bound to this antibody. In these assays, detection and quantification is carried out directly or indirectly in a known manner. Thus, detection and quantification of the antigen-antibody complexes is made possible by using suitable labels which may be carried by the antibody directed against CD36 and/or by a secondary antibody directed against the primary antibody. Depending on the type of the abovementioned immunoassays, the labels are, for example, radioactive labels, a chemiluminescent label, fluorescent dyes or else enzymes, such as phosphatase or peroxidase, which can be detected and quantified with the aid of a suitable substrate.

In one embodiment of the invention, the immunological method is carried out with the aid of a suitable solid phase. Suitable solid phases which may be mentioned include the customary commercial microtiter plates made of polystyrene or membranes (for example made of polyvinylidene difluoride, PVDF) which are customarily used for the ELISA technique.

To carry out a process according to the invention, a suitable sample, such as a liquid patient sample is applied to the solid phase. The sample is preferably a plasma sample wherein the CD36 or fraction thereof is present in unbound form or is present in a form which could be bound to its ligand LDL. The assumption herein that sCD36 is present in complex with a high molecular fraction in plasma implies that it is preferred to freeze and thaw the samples to be tested, such that said high molecular complex (lipid-protein complex) possibly is degraded.

The inventor of the present invention has shown that CD36 or an immunological reactive fraction thereof is present in a cell-free plasma sample and can be detected and quantified using a simple immunological assay and correlated with the risk of developing or the presence of various disease states which is described herein and specifically in the examples and claims below. In addition the inventor has shown that the measured relative level of CD36 present in a plasma sample is linearly correlated with fasting plasma glucose and HbA1c in DM2 patients and there is a negative linear correlation with GINF (glucose infusion rate) during a hyperinsulinemic, euglycemic clamp implying an inverse relation to insulin sensitivity. Furthermore, the inventor has shown that circulating IL-6 can be independently associated with sCD36 in subjects, mainly in glucose intolerant subjects. This finding, together with the positive association of fat mass and IL-6 ($r=0.20$, $p=0.03$), suggests that fat-derived IL-6 might lead to insulin resistance and increased sCD36 concomitantly, possibly as part of the low-grade inflammatory process, which is believed to be a major contributor to the development of insulin resistance and atherosclerosis.

Circulating sCD36 was positively associated with serum alanine transferase ($r=0.40$, $p=0.002$), aspartate amino transferase ($r=0.34$, $p=0.009$) and GT ($r=0.33$, $p=0.01$) in glucose-intolerant subjects but not in normotolerant subjects ($r=-0.03$, $p=0.7$, $r=0.09$, $p=0.3$, $r=0.05$, $p=0.6$, respectively), indicating that sCD36 may serve as a marker of non-alcoholic steatohepatitis.

It is found that plasma CD36 is located in a high MW complex which possibly is LDL or IDL, plasma CD36 levels in DM2 patients are 5 times the levels found in lean control subjects (non-DM2 subjects) and 1.5 times the levels found in obese non-DM2 control subjects, and plasma CD36 levels in obese non-diabetic DM2 relatives are 3 times the CD36 levels of obese controls. cf. Table 1 and Table 2. Based on these findings the inventor now presents the hypothesis that circulating CD36 based on degradation rate of CD36 expressing tissues or of CD36 itself may provide an alternative highly valuable diagnostic and/or prediction marker of conditions with altered expression of CD36, e.g. in macrophages, such as atherosclerosis and/or foam cell formation; in microvascular endothelium, such as microangiopathy; in platelets, such as conditions with increased platelet activation caused by dyslipidemia; or combined, such as atherothrombosis; in myeloproliferative disorders, cf. Salah-Uddin, H., Mol Cell Biochem 2002:239:203-11 and Thibert, V., Br J Hematol 1995, 91:618-24. By analogy to SR-BI in reproductive disorders. Furthermore, experimental data suggests that sCD36 besides being predictive of the development and presence of disease states such as atherosclerosis also may serve as an activity marker for these disease states, i.e. the higher the concentration of sCD36 the more "active" is the disease state. CD36 monitoring may be of diagnostic or predictive value as a signal protein from adipocytes, or degradation of CD36 on adipocytes as an adiposity signal; as a signal protein from skeletal muscle cells or cardiomyocytes, or degradation of CD36 from these cells; as a marker of flow of free fatty acids between lipoprotein fractions, such as VLDL, LDL, and chylomicrons or between lipoprotein fractions and target tissues such as skeletal or heart muscle; or based on degradation rate of CD36 expressing tissues or of CD36 itself; or as a marker for complications resulting from P. falciparum malaria, such as microvascular occlusions.

In addition it is suggested herein that circulating non-cell bound CD36 protein or fraction or fragment thereof optionally as part of a lipoprotein complex may be a useful diagnostic or predictive marker for atherosclerosis and/or atherothrombosis in patients suffering from metabolic syndrome, e.g. characterized by hypertension, insulin resistance, diabetes such as DM2, and dyslipidemia, and possibly also in patients suffering from non-alcoholic steatohepatitis, such as is characterized in steatosis hepatis with slight liver affection and insulin resistance. Both conditions showing insulin resistance, while metabolic syndrome is associated with an increased risk of atherosclerosis, and the latter being a relatively new diagnosis could also be associated with late complications such as atherosclerosis and/or atherothrombosis.

Apparently, increasing body mass index has the effect of increasing the levels of circulating CD36, and diabetes has an additional increasing end effect. This may be due to obesity resulting in a certain insulin resistance, slightly raised insulin levels and normal glucose levels. Diabetes adds raised glucose level, increased insulin resistance and insulin.

For the purposes of the present invention the term "CD36" used in phrases, such as "circulating CD36", or "non-cell bound CD36", and in the claims, includes CD36 protein or a fragment thereof which is recognized by a specific antibody against CD36, such as sc5522, sc9154, and sc7309. This includes full length CD36 protein, a polypeptide or peptide fragment thereof, as well as such protein or fragment(s) thereof present in a high molecular weight plasma fraction complex comprising lipoprotein thereof all of which are preferably soluble (sCD36). The terms circulating CD36 and soluble CD36 (sCD36) may be used as synonyms herein.

The circulating CD36 may be secreted from caveolae or which is part of a microparticle comprising membrane portions originating from a caveola membrane which has been released from a cell membrane and is present in the blood circulation. Caveolae of interest in this connection may be present in the cell membrane of cells, such as adipocytes and thrombocytes.

All literature and patent references herein are incorporated by reference including the following selected references on CD36:

1. Daviet, L. et al. 1996. Platelets 7:117-124.
2. Greenwalt DE, Lipsky RH, Ockenhouse CF, Ikeda H, Tandon NN, Jamieson GA Membrane glycoprotein CD36: a review of its roles in adherence, signal transduction, and transfusion medicine. Blood 1992 80:1105 PubMed.
3. Krieger M, Herz J Structures and functions of multiligand lipoprotein receptors: macro-phage scavenger receptors and LDL receptor-related protein (LRP). Annu Rev Biochem 1994 63:601 PubMed.
4. Savill J, Fadok V, Henson P, Haslett C Phagocyte recognition of cells undergoing apoptosis. Immunol Today 1993 14:131 PubMed.
5. Armesilla AL, Vega MA Structural organization of the gene for human CD36 glycoprotein. J Biol Chem 1994 269: 18985 PubMed.
6. Asch A S, Liu I, Briccetti F M, Barnwell J W, Kwakye-Berko F, Dokun A, Goldberger J, Pernambuco M Analysis of CD36 binding domains: ligand specificity controlled by dephosphorylation of an ectodomain. Science 1993 262:1436 PubMed.
7. Endemann G, Stanton L W, Madden K S, Bryant C M, White R T, Protter A A CD36 is a receptor for oxidized low density lipoprotein. J Biol Chem 1993 268:11811 PubMed.
8. Huang M M, Bolen J B, Barnwell J W, Shattil S J, Brugge J S Membrane glycoprotein IV (CD36) is physically associated with the Fyn, Lyn, and Yes protein-tyrosine kinases in human platelets. Proc Natl Acad Sci USA 1991 88:7844 PubMed.
9. Konig H, Pfisterer P, Corcoran LM, Wirth T Identification of CD36 as the first gene dependent on the B-cell differentiation factor Oct-2. Genes Dev 1995 9:1598 PubMed.
10. Tang Y, Taylor K T, Sobieski D A, Medved E S, Lipsky R H Identification of a human CD36 isoform produced by exon skipping. Conservation of exon organization and pre-mRNA splicing patterns with a CD36 gene family member, CLA-1. J Biol Chem 1994 269:6011 PubMed.
11. Yamamoto N, Akamatsu N, Sakuraba H, Yamazaki H, Tanoue K Platelet glycoprotein IV (CD36) deficiency is associated with the absence (type I) or the presence (type II) of glycoprotein IV on monocytes. Blood 1994 83:392 PubMed.

EXAMPLES

ELISA Analysis, Reagents Used and Assay Conditions
  Phosphate buffer 0.1 mol/l, pH 8.0
  $Na_2HPO_4$, $2H_2O$, 0.1 mol/l, pH 8.0, stored at 4° C.
POD Buffer
  $NaH_2PO_4$, $H_2O$, 1.5 mmol/l
  $Na_2HPO_4$, $2H_2O$, 8.5 mmol/l
  NaCl 400 mmol/l
  pH 7.4
  Stored at 4° C.
Preparation of Lysozyme Solution:
  Lysozyme, Sigma L-6876, 20 mg/ml. Stored at −20° C. in 1 ml portions, storage life 1 year. Storage life at 4° C. is 4 days.
POD-Avidin Dako P364: Colour Reagent
  TMB Microwell Peroxidase Substrate (1 component)
  Cat. No. 50-76-06, Kirkegård and Perry Laboratories. Storage life 1 year at 2-25° C.
Phosphoric Acid, 1 mol/l
POD-Avidin Solution:
  POD buffer 12 ml
  Lysozyme solution 120 µl
  POD-avidin 6 µl
  To be prepared immediately before use.
Antibody
  Anti-CD36: biotinylated sc-9154 (rabbit polyclonal antibody from Santa Cruz)
Apparatus
  Automatic microtiter plate-rinser Elx50 (Biotek Instruments).
  A microtiter plate is rinsed 3 times with 340 µl rinsing buffer pr. well using program 12. The last rinse is terminated without aspiration of rinsing buffer, which is first decanted immediately before application of standards (EDTA-plasma pool) and samples (with possible controls), and immediately before addition of reagent 5.

Standards

EDTA blood from 100 subjects from the routine blood sampling are centrifuged at 3000 G for 10 min, the upper part of the plasma is pipetted off and pooled. Pool-plasma is frozen in aliquots of 350 µl. (Controls in the form of platelet membrane preparations).

The intra assay coefficient of variation, which was estimated from a run of 76 single determinations of the same sample, was 10%, and estimated from double determinations of the high control on 15 different days was 6%. The inter assay coefficient of variation, estimated from the controls in each run performed, was 16.4%. Runs were only accepted when controls were within the range of +/−1.96×SD (inter assay).

Method for Elisa Assay

A microtiter plate is rinsed on the Elx50. Standards, controls, samples and dilution buffer are applied in double rows, 100 µl/well. The positions of the applications are noted. The microtiter plate is covered with plastic film and incubated for 60 min. on a shaking table.

The plate is rinsed on the Elx50. 100 µl biotinylated sc-9154 is added per well, covered with plastic film and incubate 60 min on a shaking table. The plate is rinsed on the Elx50.

100 µl POD-avidin solution is added per well. Covered with plastic film and incubate for about 30 min. on a shaking table. The plate is rinsed on the Elx50. In a fume hood 100 µl TMB is added per well. Cover with plastic film, incubate for about 10 min. on a shaking table. The reaction is terminated with 100 µl phosphoric acid per well (in a fume hood). Cover with plastic film until reading.

Measurement

Read the extinctions at 450 nm and 620 nm on a Multiscan apparatus before 60 min following the termination of the reaction.

Calculation

Cubic spline with linear scale on both axes.

Elisa dilution buffer: phosphate buffer 10 mmol/l with 0.145 mol/l NaCl, pH 7.4

Study 1: Comparison of plasma CD36 levels in obese patients with diabetes type 2, weight matched non-diabetic controls and lean non-diabetic controls.

The aim of study 1 was to compare CD36 levels in plasma from obese patients with diabetes type 2 with age and weight matched healthy controls as well as lean healthy control subjects. Our initial hypothesis was that soluble CD36 would be upregulated in diabetes as a consequence of increased glucose levels resulting in elevated expression levels in macrophages. The study subjects were carefully selected in order to match for age, gender, and BMI in the case of the obese controls and DM2 patients. Characteristics of the study population are given below in tables 1 and 2.

TABLE 1

DM2 vs. lean and obese controls

|  | Lean control | Obese control | Obese DM2 |
| --- | --- | --- | --- |
| Age | 50.8 ± 1.0 | 48.1 ± 1.5 | 49.9 ± 1.5 |
| Gender (F/M) | 5/5 | 5/6 | 6/4 |
| BMI (kg/m²) | 24.2 ± 0.5 | 34.0 ± 1.4 | 33.5 ± 1.1 |
| Fp-glucose Mmol/l | 5.7 ± 0.1 | 5.7 ± 0.2 | 10.0 ± 0.6 |
| HbA1c % | 5.5 ± 0.1 | 5.4 ± 0.1 | 7.5 ± 0.5 |

TABLE 2

Lipid parameters in study of DM2 vs. lean and obese controls

|  | Lean control | Obese control | Obese DM2 |
| --- | --- | --- | --- |
| Cholesterol mmol/l | 5.3 ± 0.2 | 5.3 ± 0.4 | 5.4 ± 0.4 |
| HDL-cholesterol | 1.85 ± 0.15 | 1.54 ± 0.15 | 1.36 ± 0.03 |
| LDL-cholesterol | 2.9 ± 0.2 | 3.2 ± 0.3 | 3.3 ± 0.3 |
| TG mmol/l | 1.12 ± 0.16 | 1.34 ± 0.18 | 1.93 ± 0.4 |

Figure 1:
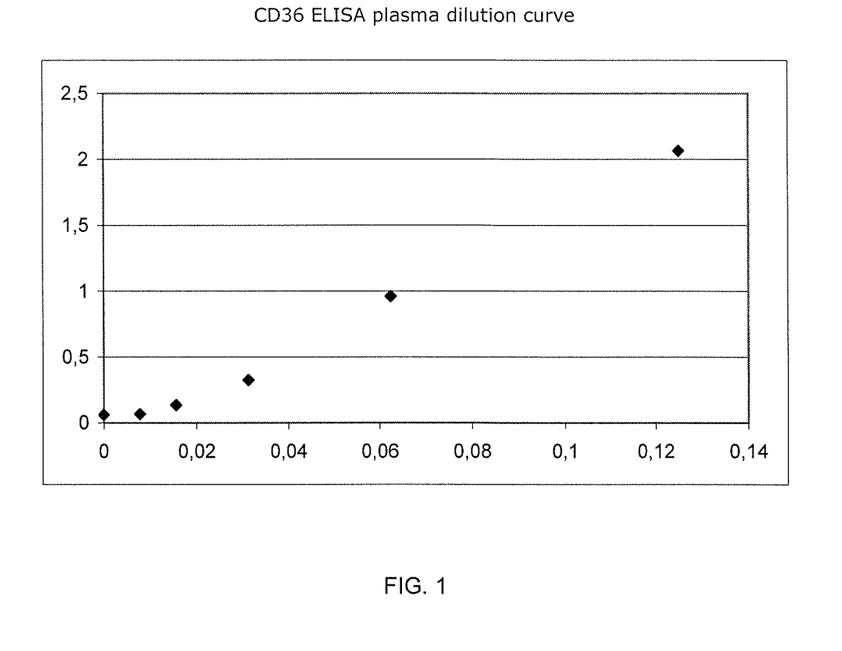
FIG. 1 shows a CD36 ELISA plasma dilution curve obtained by measuring CD36 (y-axis) in decreasing dilutions of pooled plasma. (x-axis). The background is low which secures measurements in the lower range, and the dilution curve is approximately linear over a 10 fold dilution range, which is advantageous because samples from a population with a high inter-individual variation can be measured without time-consuming measurements of additional dilution of samples.
Figure 2:
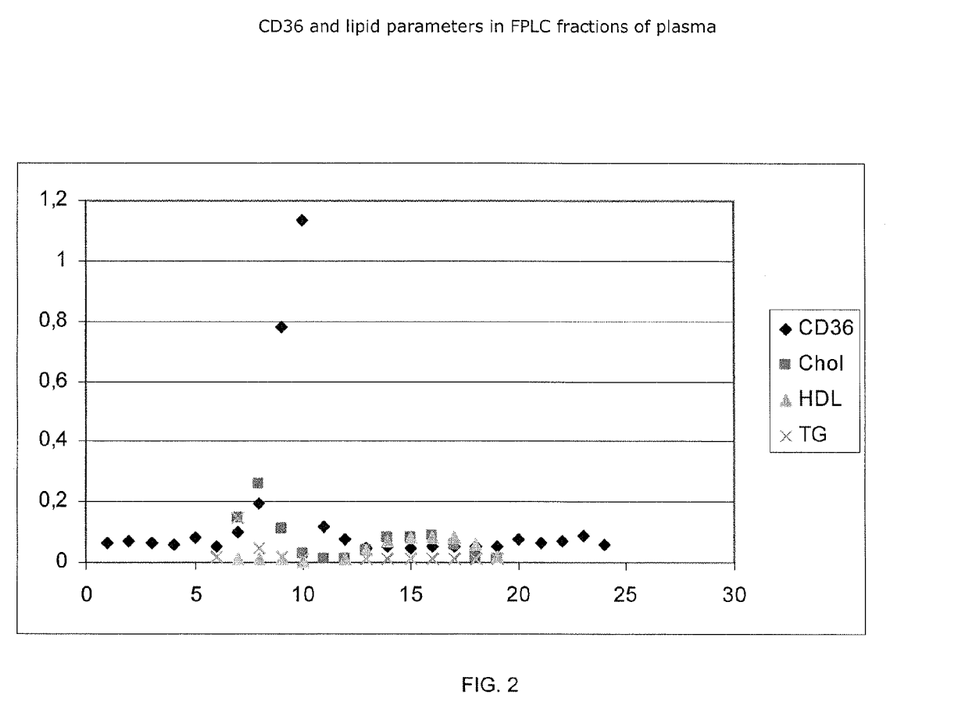
FIG. 2 shows CD36 and 3 lipid parameters (Chol=cholesterol; HDL; and TG=triglycerides) (y-axis) in FPLC fractions of plasma (x-axis). The curve for CD36 peaks together with a cholesterol fraction.
Figure 3:
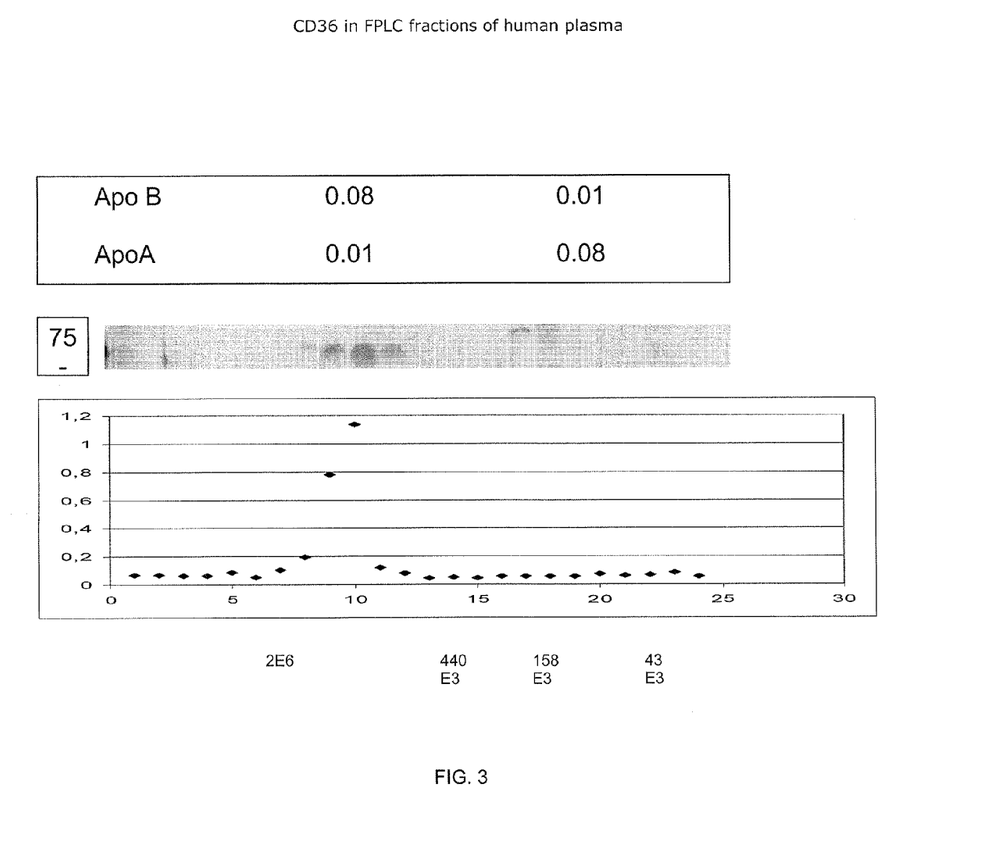
FIG. 3 shows CD36 measured by ELISA (y-axis, lower panel) in FPLC fractions of human plasma (x-axis). It can be seen from the curve that the content of CD36 peaks in fractions 9 and 10 representing molecules/particles of around 1 million gram/mol (mw-markers on lower x-axis), which is an indication of the 88 kD CD36 molecule being present in a much larger complex. The analysis of fractions 9 and 10 for ApoB and ApoA shows that the CD36 concentration is 0.08 g/l for ApoB and only 0.01 g/l for ApoA whereas the fractions 15 and 16 show the inverse relationship (upper panel) indicating that CD36 is present in the same FPLC fractions as is LDL cholesterol. Middle panel shows western blots of CD36 in FPLC fractions.
Figure 4:
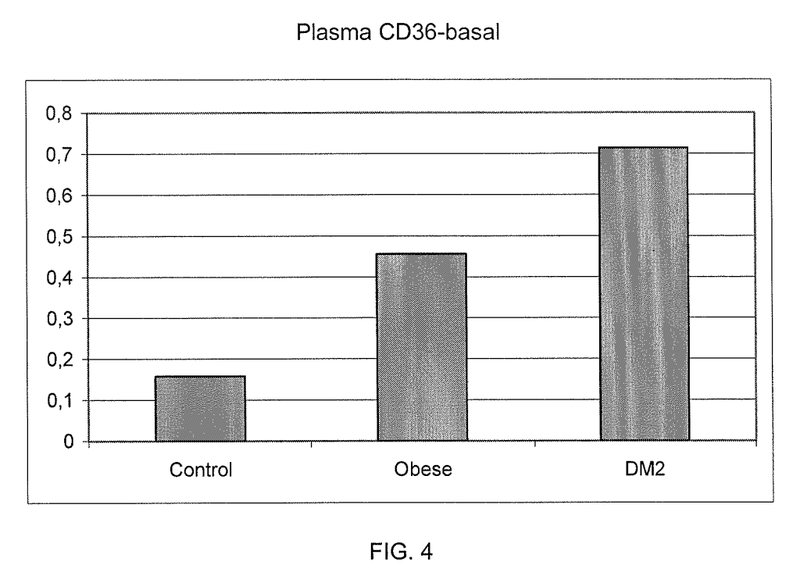
FIG. 4 shows a diagram of basal (fasting) plasma CD36 concentrations measured in arbitrary units with SEM intervals as indicated from study 1 herein. The columns show a significant difference between the basal CD36 measured in plasma from obese type 2 diabetic subjects ($p<0.0005$), and obese ($p<0.02$) compared to lean control subjects, cf. also Table 1.
Figure 5:
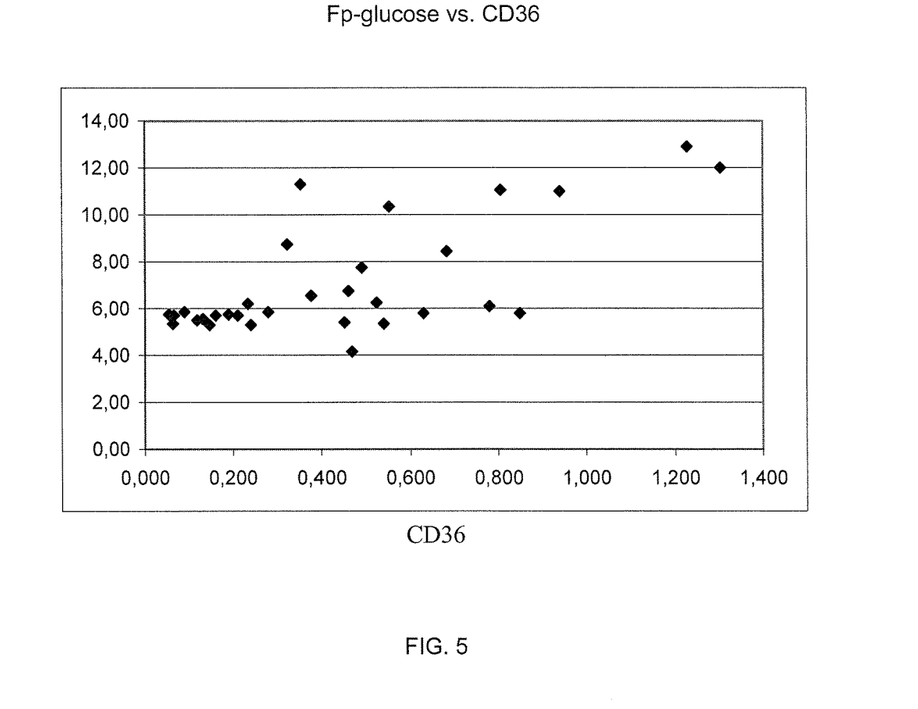
FIG. 5 is a chart showing plasma CD36 concentration (arbitrary units are used) versus fasting plasma glucose (Fp-glucose) concentration (mmol/l). Plasma CD36 was significantly correlated with fasting plasma glucose, ($r=0.69$, $p<0.0001$).
Figure 6:
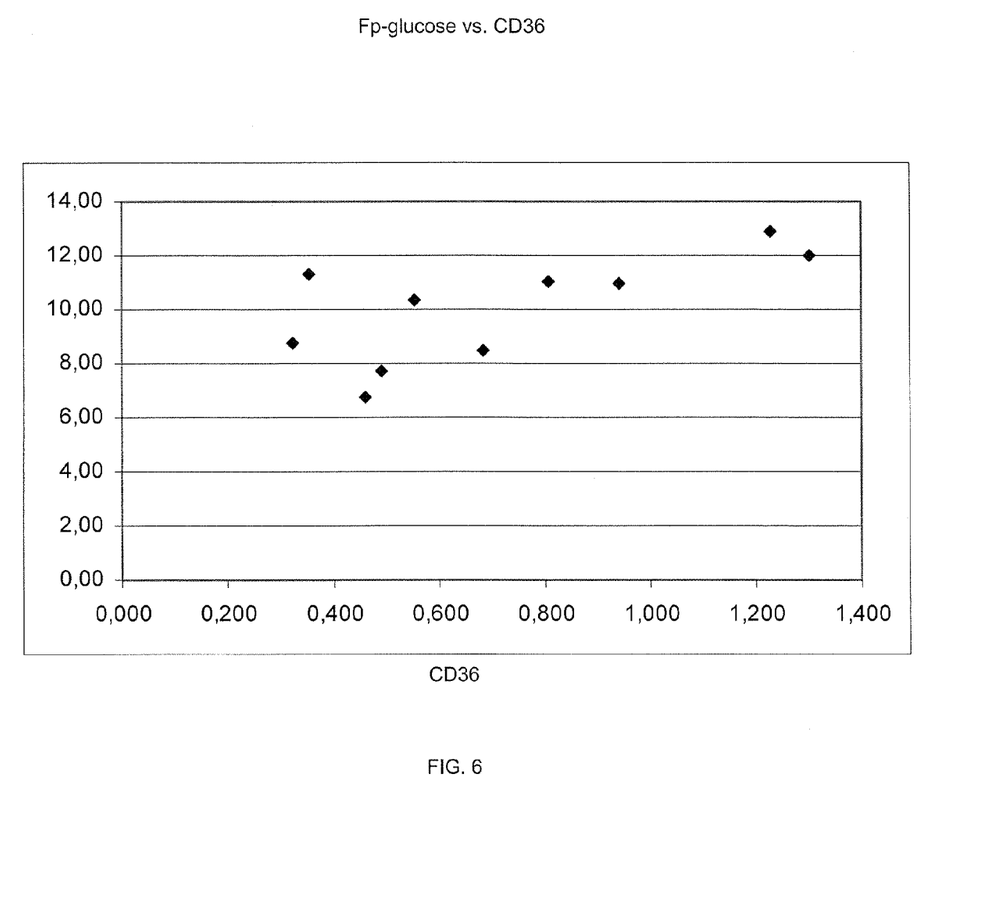
FIG. 6 is a chart showing plasma CD36 concentration (arbitrary units are used) versus Fp-glucose (mmol/l) in DM2 patients. The chart shows a consistent correlation between high plasma CD36 and raised level of Fp-glucose ($r=0.69$, $p<0.03$).
Figure 7:
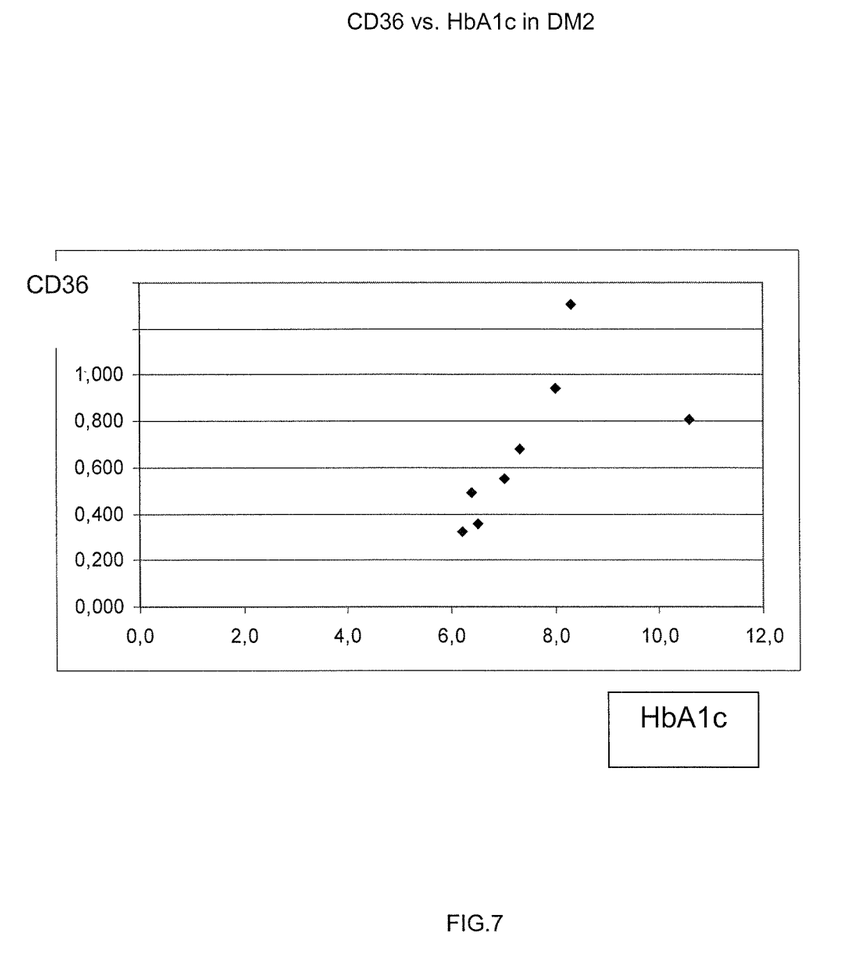
FIG. 7 is a chart showing HbA1c concentration (%) versus plasma CD36 concentration (arbitrary units are used) in DM2 patients. The chart shows a positive, and approximately linear, correlation between plasma CD36 concentrations and HbA1c concentrations (%) ($r=0.76$, $p<0.0001$).
Figure 8:
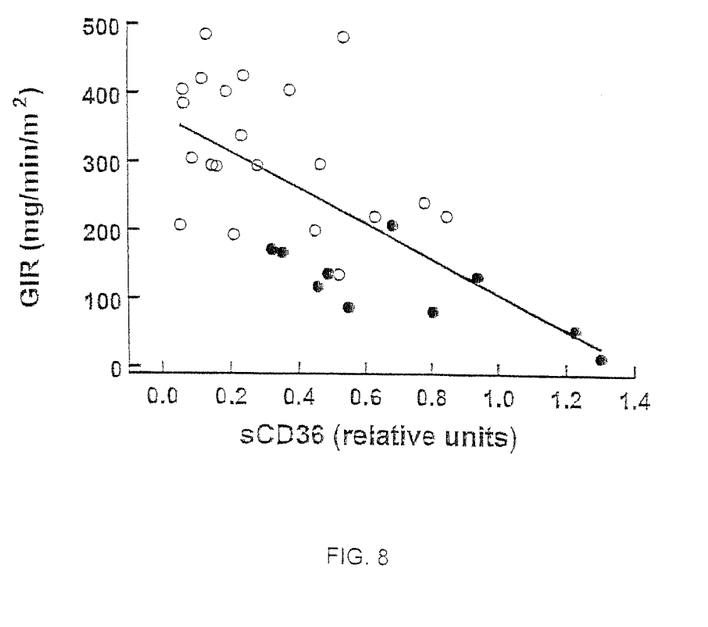
FIG. 8 is a chart showing a correlation analysis of sCD36 (soluble CD36, plasma CD36) and glucose infusion rates during euglycemic-hyperinsulinemic clamp in Study 1. Insulin sensitivity was measured as glucose infusion rates (GIR) at the end of a 3 h euglycemic-hyperinsulinemic clamp at an insulin infusion rate of 40 mU/m2 per min. sCD36 (x-axis) is plotted against GIR, black circles represent type 2 diabetic patients, open circles represent obese and lean control subjects. sCD36 and GIR were inversely correlated ($r=-0.67$, $p<0.0001$, $N=31$). The chart shows an inverse relationship between plasma CD36 and insulin sensitivity.

Blood samples to be used for determination of CD36 in plasma were obtained in 8 ml EDTA-stabilized blood sampling tubes, and centrifuged at 3000 G at 4° C. in order to obtain plasma. The plasma was immediately frozen at −80° C. until analysis. Blood samples were obtained after an overnight fast (basal samples), and again after 3 hours of insulin infusion at a rate of 40 mU/m2/min together with infusion of glucose at rates necessary to maintain euglycemia (5 mmol/l glucose). The euglycemic clamp was used to determine insulin sensitivity expressed as glucose disposal rate (mg/min/m2). Plasma samples were analysed analyzed for CD36 content as follows: The samples were thawed on ice. A 96 well microtiter plate was used. As standard pooled plasma was applied in the following dilutions: 1:2, 1:4, 1:8, 1:16, 1:32, 1:64 and 1:128 in double determinations. As background PRA sample dilution buffer was applied to 2-4 wells. Samples were applied in double determinations diluted 1:5. CD36 "concentration" was expressed in arbitrary units—relative to the pooled plasma standard. The first experiment was used to establish optimal dilution for each sample (i.e. with an expected absorption within the linear part of the standard curve). Afterwards, all the basal samples were analyzed on one ELISA plate. The results are shown in FIG. 4. Statistical analysis was performed by a two tailed T-test. Plasma CD36 was significantly higher in obese compared to controls and DM2 CD36 was significantly higher than both obese and lean controls. There was no gender difference. Plasma CD36 covariates with fasting-plasma glucose, HbA1c and most consistingly inversely with insulin sensitivity expressed as glucose disposal rates or GINF, cf. FIGS. 5, 6, 7 and 8, respectively. Analyses of covariation was expressed as Pearson's coefficient. The insulin stimulated samples were analyzed pairwise with the corresponding basal samples in double determinations, and results were expressed relative to standard pool plasma. There was observed no statistically significant effect of 4 hour insulin infusion on plasma CD36.

Study 2: CD36 in plasma from obese DM2 patients, obese young relatives of DM2 patients and obese control persons. The aim was to test the finding of elevated CD36 in DM2 patients as well as to test whether healthy persons at risk of developing DM2 express some of the CD36 findings from persons with overt DM2. Characteristics of study groups are shown in Table 3 and 4 below:

TABLE 3

Characteristics of participants in study 2

|  | Control persons | DM2 relatives | DM2 |
| --- | --- | --- | --- |
| Age (yrs) | 55 ± 3 | 26 ± 4 | 52 ± 1 |
| Gender (f/m) | 2/11 | 1/4 | 4/17 |
| BMI (kg/m²) | 31 ± 1 | 30 ± 2 | 31 ± 1 |
| Fp-glucose (mmol/l) | 6.0 ± 0.1 | 6.1 ± 0.4 | 11.4 ± 0.7 |
| HbA1c (%) |  | 7.3 ± 0.3 |  |

TABLE 4

Lipid characteristics of participants in study 2

| DM2 | | Relatives | Controls |
|---|---|---|---|
| Cholesterol (mM) | 5.6 +/− 0.2 | 4.9 +/− 0.2* | 6.1 +/− 0.2 |
| HDL (mM) | 1.1 +/− 0.1* | 1.1 +/− 0.1 | 1.4 +/− 0.1 |
| LDL (mM) | 3.6 +/− 0.2* | 2.8 +/− 0.3* | 4.2 +/− 0.2 |
| Tg (mM) | 2.3 +/− 0.3* | 2.4 +/− 0.7* | 1.2 +/− 0.1 |
| FFA (mM) | 0.65 +/− 0.05* | 0.45 +/− 0.06 | 0.40 +/− 0.03 |

TABLE 5

Antropometric data, and laboratory measurements on blood from the study participants of Study 2.

| | Control subjects | First degree relatives of type 2 diabetic patients | Type 2 diabetic patients |
|---|---|---|---|
| Gender (female/male) | 2/11 | 9/13 | 4/17 |
| Age (years) | 54.7 ± 2.7 | 30.6 ± 1.4 $^A$ | 52.4 ± 1.3 $^C$ |
| BMI (kg/m$^2$) | 31.0 ± 1.2 | 30.4 ± 0.8 | 30.5 ± 0.9 |
| Plasma glucose (mmol/l) * | | | 11.4 ± 3.3 |
| HbA1c (%) | | | 7.3 ± 1.5 |
| Plasma glucose (mmol/l) | 6.0 ± 0.1 | 5.9 ± 0.1 | 5.8 ± 0.2 |
| Serum insulin (pmol/l) | 49.6 ± 8.8 | 73.1 ± 6.8 | 161.8 ± 16.4 $^{A, C}$ |
| Free fatty acids (mmol/l) | 0.40 ± 0.03 | 0.46 ± 0.04 | 0.27 ± 0.04 $^{B, C}$ |
| Triglyceride (mmol/l) | 1.2 ± 0.1 | 1.8 ± 0.2 $^B$ | 1.9 ± 0.2 $^A$ |

Values are mean ± SE.
* Fasting plasma glucose and HbA1c were measured one day prior to the euglycemic-hyperinsulinemic clamp in type 2 diabetic subjects. Other variables were measured in the basal state during the clamp studies.
$^A$ P < 0.01 and
$^B$ P < 0.05 vs. obese controls.
$^C$ P < 0.01 vs. first degree relatives.

Figure 9:
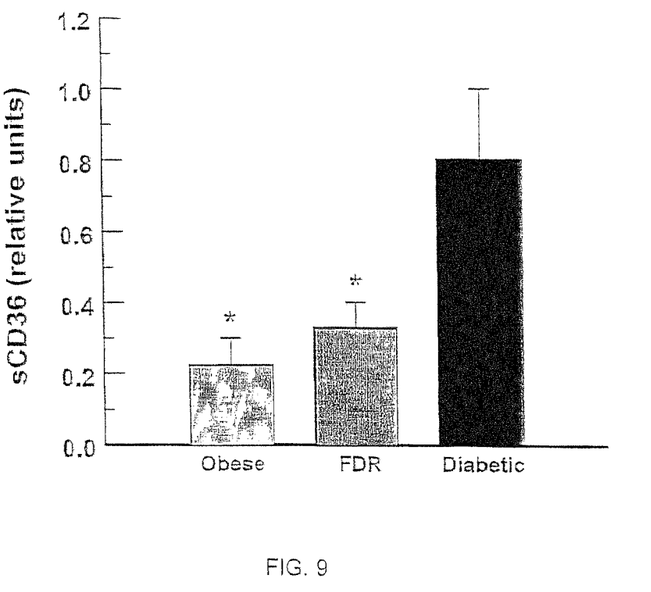
FIG. 9 shows soluble CD36 in obese controls, obese relatives and type 2 diabetic patients. Soluble CD36 (sCD36) was measured in plasma from obese type 2 diabetic subjects (Diabetic), and obese relatives (FDR) and obese control (obese) subjects by ELISA assay, and expressed relative to pooled plasma (relative units). *$p<0.025$ compared to obese type 2 diabetic patients. Study participants are described in Table 5.
Figure 10:
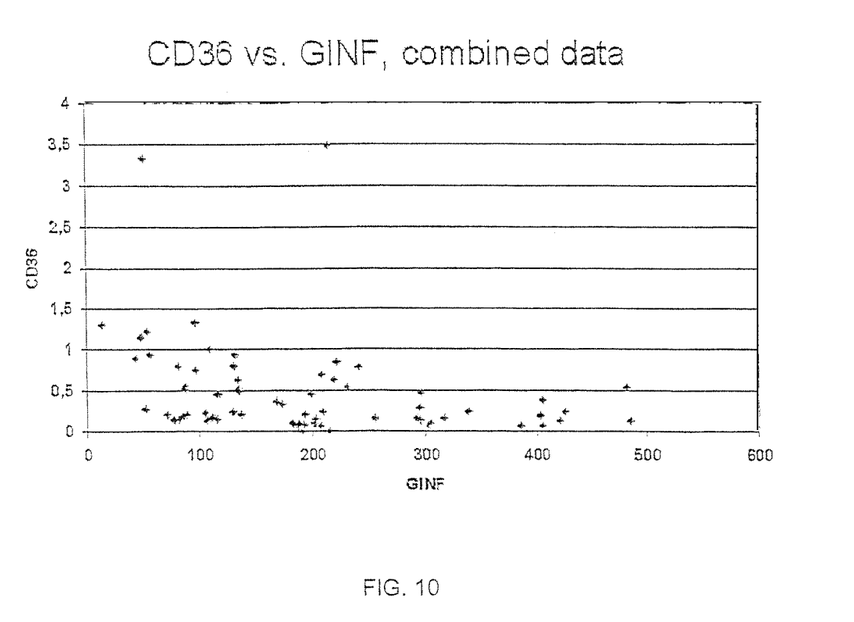
FIG. 10 is a chart showing GINF (glucose infusion rate, mg glucose/m$^2$/min) versus plasma CD36 concentration measured in arbitrary units during the last 30 min. of a 3 hour hyperinsulinemic euglycemic clamp with an insulin infusion rate of 40 mU/m$^2$/min. The chart shows an inverse relationship between plasma CD36 and insulin sensitivity including subjects characterized in tables 1 to 4.

Basal control samples from DM2 patients were obtained 1-2 days ahead of study. Patients with DM2 were admitted to hospital the night before, and plasma glucose was normalized overnight by insulin. CD36 was measured as described in study 1 in fasting basal samples. CD36 was significantly elevated in DM2 patients compared to relatives and weight matched controls, cf. FIG. 9. Plasma CD36 was correlated with glucose infusion rate during a 3 hour euglycemic hyperinsulinemic clamp performed as described in study 1, cf. FIG. 10.

Study 3

There is increasing evidence that systemic inflammation and insulin resistance constitute interrelated events that contribute to atherosclerosis. We studied the effect of the association between circulating interleukin 6 (IL-6) levels, one of the major mediators of inflammation, and insulin resistance on sCD36.

We aimed to study this relationship in 147 apparently healthy men, 90 normotolerant and 57 glucose-intolerant subjects.

When all subjects were considered as a whole, circulating sCD36 concentration was significantly associated with fat-free mass, glycosylated hemoglobin, plasma triglycerides, platelet number, plasma interleukin 6 and with glucose effectiveness (p between 0.04 and 0.001). However, the association with fat-free mass, triglycerides, platelet number and interleukin 6 was mainly observed in subjects with glucose intolerance but not in normotolerant subjects.

Circulating sCD36 was negatively associated with fasting glucose and positively with glucose effectiveness in normotolerant subjects. In subjects with glucose intolerance, sCD36 was positively associated with fasting glucose and negatively with insulin sensitivity.

In a multiple linear regression analysis to predict circulating sCD36, In all subjects considered as a whole, IL-6 (p=0.033) and fat-free mass (p=0.035) independently contributed to 5% and 5%, respectively, of sCD36 variance, after adjusting for age, fasting glucose, plasma triglycerides, platelet count and insulin sensitivity.

Among subjects with glucose intolerance, IL-6 (p=0.0035) and fat mass (p=0.025) were independently associated with plasma sCD36 concentration, contributing to 12% and 9%, respectively, of sCD36 variance after adjusting for the same variables.

Thus, circulating IL-6 was independently associated with sCD36 in all subjects, mainly in glucose intolerant subjects. This finding, together with the positive association of fat mass and IL-6 (r=0.20, p=0.03), suggests that fat-derived IL-6 might lead to insulin resistance and increased sCD36 concomitantly, possibly as part of the low-grade inflammatory process, which is believed to be a major contributor to the development of insulin resistance and atherosclerosis.

Circulating sCD36 was positively associated with serum alanine transferase (r=0.40, p=0.002), aspartate amino transferase (r=0.34, p=0.009) and GT (r=0.33, p=0.01) in glucose-intolerant subjects but not in normotolerant subjects (r=−0.03, p=0.7, r=0.09, p=0.3, r=0.05, p=0.6, respectively), indicating that sCD36 could serve as a marker of non-alcoholic steatohepatitis.

The invention claimed is:

1. A method of predicting an increased risk of a patient developing a disease state where said disease state belongs to the group of diseases consisting of atherosclerosis, atherothrombosis, microangiopathy, metabolic syndrome, non-alcoholic steatohepatitis, insulin resistance, diabetes, and combinations thereof, wherein said method comprises the steps of:
(a) obtaining a cell-free plasma sample from said patient, the cell-free plasma sample comprising a lipoprotein fraction in or in addition to high molecular weight complexes capable of being disrupted by freezing and thawing the sample;
(b) contacting the sample with an anti-CD36 antibody to obtain a CD36-antibody complex, wherein said anti-CD36 antibody is selected from the group of antibodies consisting of monoclonal anti-human CD36 antibody sc-7309, rabbit polyclonal antibodies specific for amino acids 1-300 of human CD36, and goat polyclonal antibodies specific for an N-terminal peptide of human CD36;

(c) incubating said sample with said antibody to obtain a CD36-antibody complex;

(d) contacting said complex with a labelled compound having specific binding affinity for said complex;

(e) detecting labelled compound bound to said complex, whereby an amount of CD36 protein present in said cell-free plasma sample comprising high molecular weight complexes is measured as indicative of a level of circulating CD36 in the patient; and (f) determining whether the CD36 level measured in step (e) is above a reference level determined from healthy subjects, an increased level of circulating CD36 in said patient above the reference level from the healthy subjects being predictive of an increased risk of the patient developing said disease state.

2. The method according to claim 1, wherein said reference level determined from healthy subjects is determined from a long term outcome study.

3. The method of claim 1, wherein the patient is selected from the group consisting of type 2 diabetes mellitus patients, obese type 2 diabetes mellitus patients, and healthy relatives of type 2 diabetes mellitus patients and non-diabetic obese persons.

4. The method of claim 1, wherein the increase in CD36 levels is at least 250% relative to the reference level of circulating CD36 in healthy subjects.

5. The method according to claim 1, wherein in step (b) said sample is contacted with said antibody bound to a solid phase.

6. The method of claim 5, wherein the solid phase is a microtiter plate.

7. The method of claim 1, wherein said anti-CD36 antibody is a polyclonal CD36 specific antibody.

8. The method of claim 1, wherein said lipoprotein fraction is selected from the group consisting of Low Density Lipoprotein, Intermediate Density Lipoprotein, and Very Low Density Lipoprotein.

9. The method of claim 1, wherein the molecular weight of said high molecular weight complexes is within 440,000-2,000,000 g/mol.

10. The method of claim 1, wherein the molecular weight of said high molecular weight complexes is around 1,000,000 g/mol.

11. A method of evaluating a presence and/or an activity and/or a degree of a disease state in a patient, where said disease state belongs to the group of diseases consisting of atherosclerosis, atherothrombosis, microangiopathy, metabolic syndrome, non-alcoholic steatohepatitis, insulin resistance, diabetes, and combinations thereof, wherein said method comprises the steps of:

(a) obtaining a cell-free plasma sample from said patient, the cell-free plasma sample comprising a lipoprotein fraction in or in addition to high molecular weight complexes capable of being disrupted by freezing and thawing the sample;

(b) contacting the sample with an anti-CD36 antibody to obtain a CD36-antibody complex, wherein said anti-CD36 antibody is selected from the group of antibodies consisting of monoclonal anti-human CD36 antibody sc-7309, rabbit polyclonal antibodies specific for amino acids 1-300 of human CD36, and goat polyclonal antibodies specific for an N-terminal peptide of human CD36;

(c) incubating said sample with said antibody to obtain a CD36-antibody complex;

(d) contacting said complex with a labelled compound having specific binding affinity for said complex;

(e) detecting labelled compound bound to said complex, whereby an amount of CD36 protein present in said cell-free plasma sample comprising high molecular weight complexes is measured as indicative of a level of circulating CD36 in the patient; and (f) determining whether the CD36 level measured in step (e) is above a reference level determined from healthy subjects, an increased level of circulating CD36 in said patient above the reference level from the healthy subjects being predictive of an increased risk of the patient having said disease state and increasing magnitude of the increased level being predictive of an increasing risk of the patient having an elevated activity and/or degree of said disease state.

* * * * *